United States Patent [19]

Traub et al.

[11] 4,214,164
[45] Jul. 22, 1980

[54] CONTROL OF SPOT WELD QUALITY BY INFRARED THERMAL SENSING

[75] Inventors: Alan C. Traub, Framingham; Riccardo Vanzetti, Walpole, both of Mass.

[73] Assignee: Vanzetti Infrared & Computer System Incorporated, Canton, Mass.

[21] Appl. No.: 926,055

[22] Filed: Jul. 19, 1978

[51] Int. Cl.² .............................................. G01J 1/00
[52] U.S. Cl. .................................... 250/338; 73/342; 250/358 R
[58] Field of Search ............... 250/338, 339, 340, 342, 250/358 R; 73/342, 355 R, 355 EM

[56] References Cited

U.S. PATENT DOCUMENTS

| | | | |
|---|---|---|---|
| 3,191,441 | 6/1965 | Erickson | 250/338 X |
| 3,868,508 | 2/1975 | Lloyd | 250/338 X |

Primary Examiner—Davis L. Willis
Attorney, Agent, or Firm—Sughrue, Rothwell, Mion, Zinn and Macpeak

[57] ABSTRACT

Control of spot weld quality is effected by observing the progress of heat generation within the weld and initiating automatic corrective action if the heating rate is initially too high or too low. A flexible optical fiber bundle has one end located in the welding tip and the other end optically coupled to an infrared detector. Due to the excellent thermal conductivity of the copper material of the welding tip, thermal energy is conducted very rapidly for a short distance into the tip during the weld formation so that the infrared detector produces an output signal proportional to the weld temperature. This signal is sampled and compared with a previously-recorded signal corresponding to the heating rate that produced a good spot weld in the material being welded.

4 Claims, 11 Drawing Figures

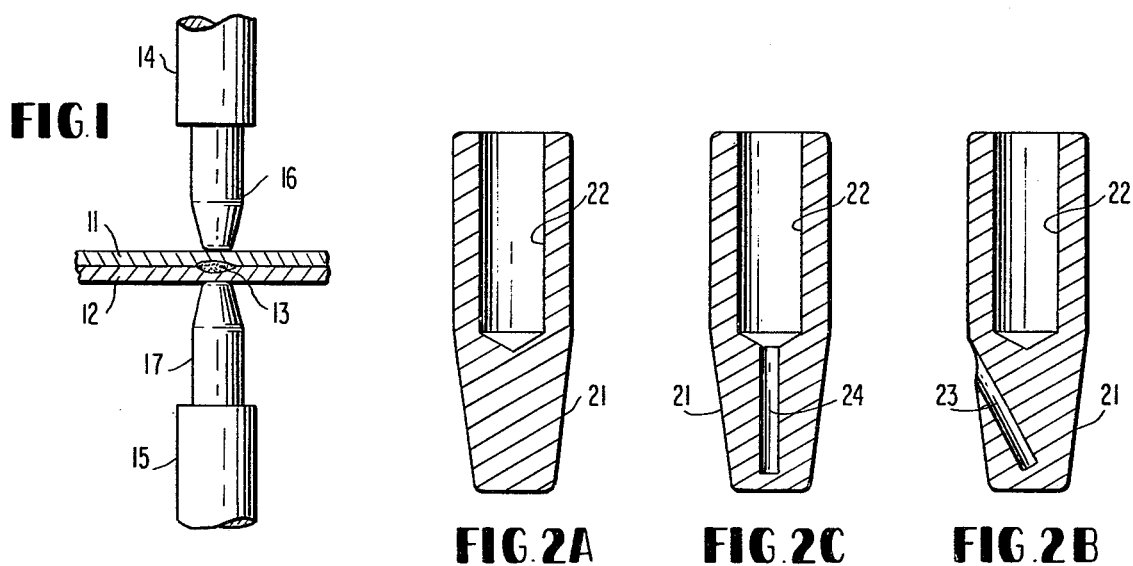
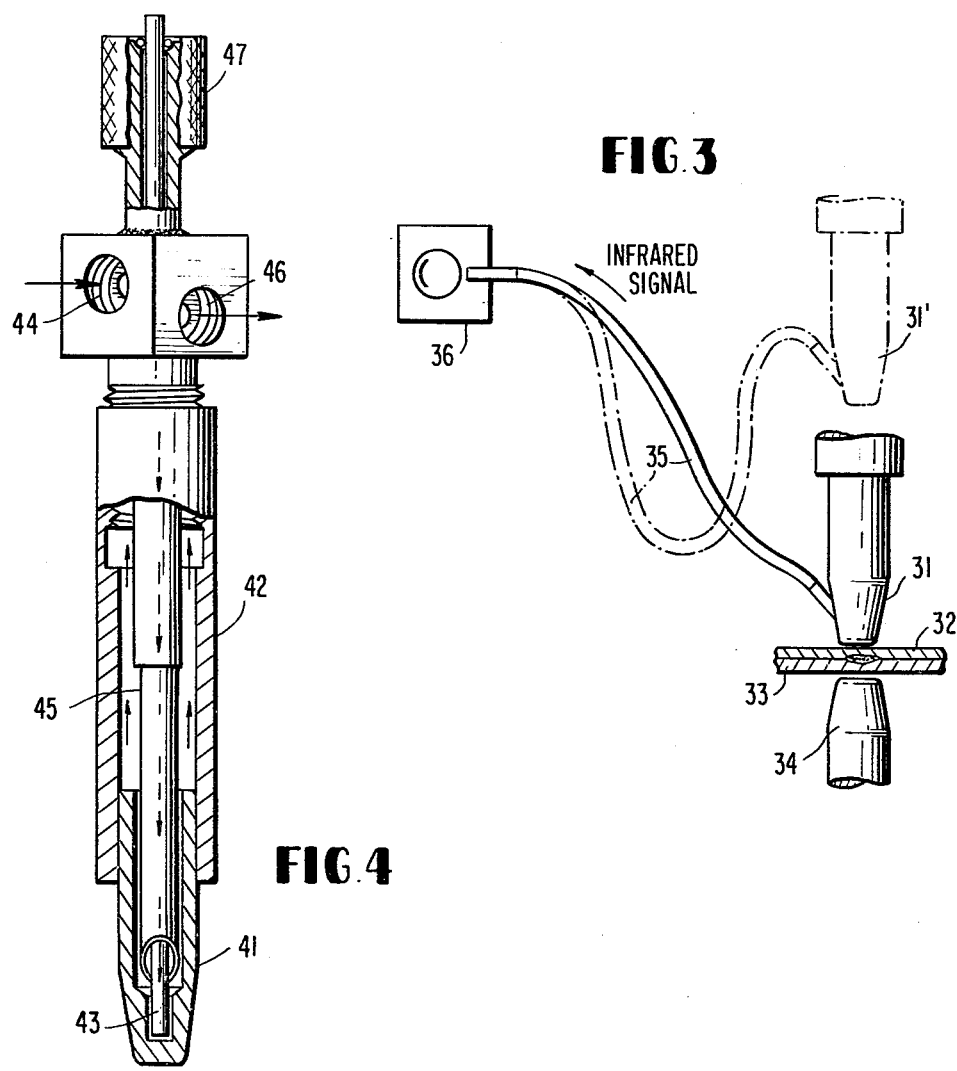

CONTROL OF SPOT WELD QUALITY BY INFRARED THERMAL SENSING

BACKGROUND OF THE INVENTION

This invention relates to the control of welding power and of welding duration, during the formation of an electrical resistance spot weld, by means of infrared temperature sensing.

In this type of spot weld as illustrated in FIG. 1, two sheets of metal 11 and 12 are joined by melting and fusing a local area 13 under high temperature and pressure. The temperature is achieved by the passage of a momentary high electrical current through the metallic sheets. The current results from the application of a low voltage by a pair of electrodes 14 and 15, usually of copper. The sheets are placed between tips 16 and 17 of the electrodes which are then brought together so as to provide both voltage and pressure.

The pressure, the welding voltage, the welding duration and other variables are under the control of the operator, via a set of panel controls on the welding machine. Once the controls have been adjusted to form a weld with the desired characteristics, they remain undisturbed if it is desired to form a series of identical welds, as in a production operation.

Most usually, however, a series of such welds will show random variations in their properties. Many unacceptable welds will be formed because the current or the pressure was too low. These will be interspersed with both normal welds and overheated welds. The latter are undesirable because they do not meet the standards of strength of appearance, they accelerate the wear of the electrode tips and they are wasteful of electrical energy.

The low-pressure welds result when the sheets are warped or buckled and resist the mechanical force of the electrodes. The low-current and overheated welds result from a variety of reasons:

Supply voltage variation;

Variation in quality and cleanliness of the work sheets;

Progressive deterioration (flattening, corrosion) of the welding tips;

Variations in the temperature or flow rate of the cooling water which circulates within the tips;

Work sheet preheatng due to nearby, previously-formed welds;

Electrical power shunting, or diversion, due to nearby, previously-made welds;

Work sheet "heat-sinking" variations, or differences in the rates at which the work sheets draw heat from the weld, depending on whether the weld is formed near the center of the sheets or near an edge or a corner; or Any condition which creates high-energy sparks which draw energy from the weld. Sparks can result from low pressures, corrosion or welding at the edge of the work sheets.

It is an accepted fact in the welding industry that these variations do occur. However, it is less practical to try to control all of these variables than it is simply to form an extra number of welds for each pair of work sheets which are to be joined. Thus, the most economical solution is to specify that a certain percentage of additional welds be formed, above the number which would be required if all welds were perfect. The extra amount varies with the welding conditions and the work-quality requirements. A typical range is from 30–100%.

Nonetheless, the extra welds are costly in terms of power, equipment wear, electrode replacement and labor. Several methods have been attempted for providing better control of the spot welding process, but none has met with wide acceptance because they are either costly or ineffective.

In one method, the amount of electrical power applied to each weld is "metered" so that the same amount of energy is expended in each weld, regardless of variations in resistance to the flow of electrical current. Thus, a weld which draws low current is heated for a longer period of time. This method uses the fact that the amount of heat produced depends upon the product of both the current (squared) and the time. Thus, a low current for a long time should provide the same heat as a high current for a short time. However, this is true for only a limited range of current values. One ampere of current for a prolonged time will not produce the same weld as 10,000 amperes for one second. This is because in low-current welds, the heating rate is not sufficient to overcome the cooling influences of the welding tips and the surrounding work sheets. Below a certain current value, the weld can never reach the fusion temperature.

Other weld-quality monitors have been proposed which are used for evaluation purposes but not for the control of the individual weld. They are "after-the-fact" methods which indicate that certain control adjustments should be made. One such method is a "thermal expansion" type in which a sensitive pressure detector monitors the amount and rate of thermal expansion as the weld is being formed. Other methods make use of acoustic emissions which occur during mechanical changes when the weld is being formed. The transmssion of ultrasonic acoustical energy through each weld, during or after formation, is another method of evaluation. As we have indicated, none of these methods is in widespread use.

SUMMARY OF THE INVENTION

The central concept of the present invention is that because the weld is formed as a direct result of heating, it is the heating which should be measured and not some other parameter. Our procedure then is to observe the progress of heat generation within the weld, instant by instant, and to initiate automatic corrective action if the heating rate is initially too low or too high. In this way, we prevent the formation of weak, low-current welds, and we also avoid the destructive effects of high-current welds.

The method makes use of the fact that during weld formation, thermal energy is conducted very rapidly for a short distance into the welding tip. The high heat-flow rate is due to the excellent thermal conductivity of the copper material. During a normal weld, the copper material within two or three millimeters of the contact surface reaches very high temperatures within a few hundredths of a second. If a hole is prepared through the top or the side of the tip so that its bottom is close to the contact face, the bottom of the hole will emit substantial infrared radiation within a short time after weld initiation. This radiation can be measured rapidly (within a few thousandths of a second) by various infrared radiation detectors which are known.

To measure the infrared radiation emitted from the bottom of the hole in the welding tip, a flexible optical fiber bundle is inserted at one end into the hole in the welding tip, and the other end is optically coupled to an infrared detector. Thus, the infrared detector produces an output signal which is proportional to the temperature of the weld. This signal is sampled at a preselected time during the beginning of the weld cycle by control circuitry.

The control circuitry has two modes: a "set-up" mode and an "automatic" mode. During the set-up mode, a test weld is made and the sampled detector signal is recorded in a set point memory. The weld is then tested by the operator by any conventional method. If the weld is not satisfactory for the material being welded, the operator makes adjustments in the welding current or time or both and makes another test weld. With each test weld, the detector signal is sampled and recorded in the set point memory, the previously-recorded signal being destroyed. When a satisfactory weld is achieved, the operator switches the control circuitry to the automatic mode, and, thereafter, the last recorded detector signal is preserved in the set point memory.

In the automatic mode, the sampled detector signal is compared with the signal last recorded in the set point memory. If the sampled thermal signal of a weld in the automatic mode is lower or higher than the signal recorded in the set point memory, the welding current is either increased or decreased and the weld proceeds at the new power level. At the end of the weld, the control circuitry is automatically reset for the next weld.

BRIEF DESCRIPTION OF THE DRAWINGS

The invention will be better understood from the following detailed description with reference to the accompanying drawings, in which:

FIG. 1 is a view in partial cross-section showing the formation of a spot weld between two work sheets under high temperature and pressure;

FIG. 2A is a cross-sectional view of a typical welding tip;

FIGS. 2B and 2C are cross-sectional views of welding tips modified according to the invention;

FIG. 3 is a pictorial view showing the use of the welding tip of FIG. 2B;

FIG. 4 is a cross-sectional view in more detail showing the use of the welding tip of FIG. 2C;

DETAILED DESCRIPTION OF THE INVENTION

Figure 4A:
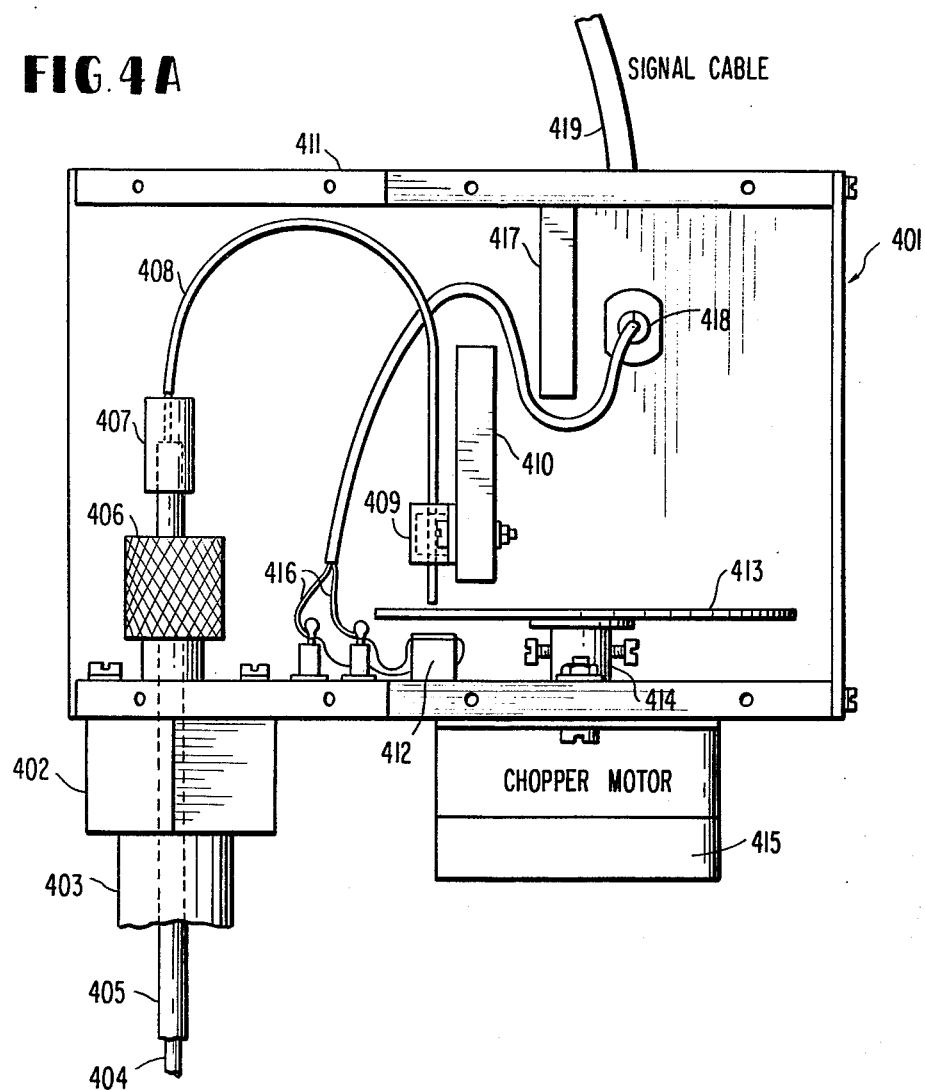
FIG. 4A is a side view of an infrared detection system for use with the welding tip shown in FIG. 4.

Referring now to the drawings and, more particularly, to FIGS. 2A–2C, a typical welding tip 21 is provided with a water hole 22 for a cooling jet. In FIG. 2B, the tip is modified by providing a side hole 23, the bottom of which is but a few millimeters from the contact face of the tip. Alternatively, the tip may be modified as shown in FIG. 2C by providing a hole 24 concentric with the water hole 22. Again, the hole 24 extends to within a few millimeters of the contact face of the welding tip. Typically, the holes 23 and 24 need be a few millimeters in diameter, and enough copper remains between the hole and the contact face so as to withstand the high tip pressure during heating.

The small hole diameter does not conveniently permit the mounting of a standard infrared detector inside or near the hole. It is therefore a feature of our invention that we "pipe" the radiation from the hole to a fixed detector via a bundle of flexible optical fibers. FIG. 3 shows one method of doing this, using the sidehole configuration illustrated in FIG. 2B. The welding tip 31 is shown in solid line in the welding position. In this position, the work sheets 32 and 33 are clamped between the welding tips 31 and 34. The welding tip 31' is shown in dotted line in the retracted position. A flexible optical fiber bundle 35 has one end fitted into the side hole of welding tip 31 and the other end optically coupled to a fixed infrared detector 36.

A second method of "piping" the radiation from the hole to a fixed detector is shown in FIG. 4. In this case which uses the welding tip shown in FIG. 2C, a rigid optical conduit 43 within the welding tip 41 and electrode 42 assembly transmits radiation via a flexible optical fiber bundle (not shown) to an infrared detector (not shown) which is mounted on top of the electrode piston. The detector therefore moves vertically with the piston. The optical transmission path is contained within the water-cooling system of the electrode, and it emerges through a pressure seal at the top. More specifically, cooling water is supplied to water inlet port 44 and is conducted through the electrode 42 via a water inlet tube 45 into the welding tip 41. The outside diameter of the inlet tube 45 is smaller than the diameter of the water hole in the welding tip so that the water returns along the outside of the inlet tube to be exhausted at outlet port 46. The dotted arrows show the supply water, and the solid arrows show the return water. The rigid optical conduit 43 passes through the inlet tube 45 and emerges through a quick disconnect seal 47.

FIG. 4A shows the design of a particular infrared detection system which we have used with the electrode assembly shown in FIG. 4. A detector head assembly 401 is mounted on top of the electrode piston by means of a clamp 402 secured to the welding electrode 403. The rigid optical conduit 404 is contained within a stainless-steel jacket 405 which passes through the disconnect seal 406. A fiber interface coupling 407 connects the rigid optical conduit 404 to a flexible optical fiber bundle 408 which is sheathed with a PVC jacket. The free end of the flexible optical fiber bundle is clamped in a fiber alignment fixture 409 mounted on a combination support bracket and light baffle 410. The support bracket and light baffle 410 is itself mounted to an interior wall of the housing 411 of the detector head assembly, it being understood that a side wall of housing 411 has been removed in the illustration for purposes of showing the components of the detector head assembly.

The fixture 409 holds the free end of the flexible optical fiber bundle 408 so that the radiation conducted by the bundle is directed toward a lead sulfide infrared detector 412. Interposed between the free end of the fiber bundle 408 and the detector 412 is the toothed edge of a copper wheel 413 which is driven through a wheel hub 414 by a chopper motor 415. Wires 416 are connected to the leads of the detector 412 and are routed over support bracket and light baffle 410 and under a second light baffle 417 before passing through a strain relief 418 in a side wall of the housing 411. The light baffle 417, like support bracket and light baffle 410, is mounted to an interior wall of the housing 411 and cooperates with baffle 410 to prevent any light leakage from strain relief 418 from reaching detector 412. After passing through the strain relief 418, the wires 416 are provided with a suitable sheath to form a signal cable 419 which connects to control circuitry to be described hereinafter.

Although lead sulfide was the choice of detector material, other detector types might have been used, as will be understood by those familiar with the detector art. The use of the copper wheel in this case is also known to infrared detection specialists as a means of overcoming room-temperature effects on the detector signal. In response to an infrared signal, the chopped detector signal provides an AC electrical output signal, typically at a frequency in the 400–1000 Hz range in this case, depending upon the chopper.

Summarizing the operation, during weld formation, shortly after welding is begun, heat is transferred from the faying surfaces to the top of the upper work sheet and then into the upper welding tip. Infrared radiation is transmitted via the optical fibers to the optical detection head. Within the detection head assembly, the radiation leaves the fibers and passes through a toothed motor-driven chopper wheel. The radiation is interrupted and then falls on the lead sulfide detector. Here, it is converted to an alternating electrical signal which may then be processed in the normal manner, being finally converted to an amplified, filtered DC signal. This is the signal which is used by the logic circuit of the control circuitry in order to carry out any needed welding power correction and to interrupt the power when required.

Figure 5:
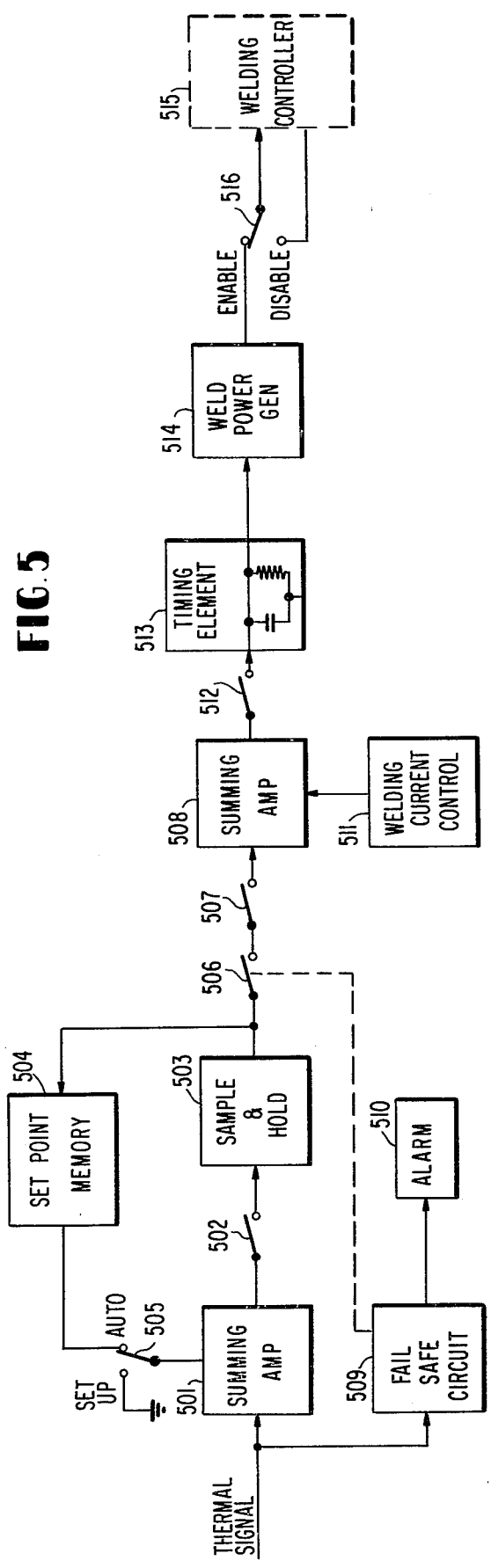
FIG. 5 is a block diagram of the control circuitry according to the invention.

FIG. 5 shows the functional block diagram of the control circuitry and comprises an input summing amplifier 501 which receives at its non-inverting input the filtered DC signal derived from the detection head assembly. The output of amplifier 501 is supplied to a sample switch 502 at the input of a sample and hold circuit 503. The output of the sample and hold circuit 503 is supplied to a set point memory 504 which is preferably composed of an analog-to-digital converter, a solid-state digital memory and a digital-to-analog converter. The sampled analog voltage is stored as a digital value, and this digital value is converted back to an analog voltage by the set point memory, thereby avoiding the drift problems associated with long-term analog memories. The analog output voltage from the set point memory is supplied to the mode selector switch 505, which, in the "automatic" position, supplies the output voltage to the inverting input of summing amplifier 501.

The sampled analog voltage from sample and hold circuit 503 is also supplied to series connected switches 506 and 507, which, when both are closed, supply the sampled voltage to the non-inverting input of a second summing amplifier 508. Switch 506 serves two functions. In the set-up mode, switch 506 is open to prevent the sampled analog voltage from having any effect on the welding operation. In the automatic mode, switch 506 is normally closed but will be opened by the operation of fail-safe circuit 509. The fail-safe circuit receives as its input the filtered DC signal derived from the detection head assembly. If the input signal does not reach a preset threshold within a predetermined period of time, the fail-safe circuit operates to open switch 506 to ensure that no control action is taken, and, at the same time, the operator is notified via an alarm 510 that a low thermal signal was received. The fail-safe circuit 509 is automatically reset after each weld.

Switch 507 is normally open but closes just after switch 502 opens, thereby supplying a correction signal to summing amplifier 508. The inverting input to amplifier 508 is connected to a manually adjustable welding current control potentiometer 511. The output of amplifier 508 is supplied via switch 512 to timing element 513. Switch 512 is normally open but closes just before zero crossings of the welding current to "sample" the output of amplifier 508, which is used to charge the capacitor in the timing element 513. Switch 512 then opens at a zero crossing of the welding current, allowing the capacitor voltage to decay toward zero.

When the voltage from the timing element 513 decays to a predetermined level, the weld power generator 514 is turned on for the remainder of that half-power cycle, causing, in a well-known manner, one or the other of two ignitrons (not shown) to fire, depending on whether a positive or a negative half-cycle is in progress. The output of the weld power generator is supplied to a conventional welding controller 515 containing the ignitrons.

System operation is begun with the mode selector switch in the "set-up" position so that the only signal which enters summing amplifier 501 is the thermal signal. The weld drive switch 516, shown at the input to the welding controller 515, is in the "enable" position. This switch is provided for convenience in electrically disengaging the control circuitry from the welding machine.

The sequence is begun when a weld is made and when a thermal signal enters summing amplifier 501. At the same time, the thermal signal enters the fail-safe circuit 509 and is sampled at the end of the sample time. The sample time is selected by the operator via a pair of thumb-wheel switches (not shown). These switches determine the time duration, in current cycles, after which the system must "decide" whether to make a power correction or not, when it is in the automatic mode. The sample time comprises a small portion of the welding time, just long enough that the thermal signal is safely above the threshold during a normal weld. The sample switch 502 is closed during the sample time and it opens automatically afterward.

When the sample switch 502 opens, the signal value from summing amplifier 501 is registered by the sample and hold circuit 503 and is diverted to the set point memory 504 where it is stored as a digital value. Being stored digitally, its value will be retained indefinitely until it is replaced by a new value or until the system power is turned off.

With the mode selector switch 505 in the set-up position, no further action is taken by the system other than the storage of the sampled voltage value. Switch 506 is in the open position and isolates the sampling function from the control function. The weld proceeds normally to its conclusion as determined by the duration control (not shown) on the welding machine controller 515. When a new weld is made, under different conditions, a new sampled voltage value is stored in the digital memory. There, it is retained for later use when the operator decides that the weld is satisfactory and that automatic operation should be initiated.

In the set-up mode, the welding power is controlled via the welding current control potentiometer 511. The voltage from this control is the only one to enter summing amplifier 508 during set-up operation. It replaces the function of the current control on the welding machine controller, thereby disabling it. However, it operates in exactly the same way by determining just when, during each power pulse, an ignitron should fire in order to apply power to the weld. For high welding power, a low voltage value proceeds from the welding current control 511. This places a smaller charge in the capacitor in the timing element 513, which, therefore, decays to the threshold value sooner, firing the ignitron earlier. The power cycle is interrupted at the next zero crossing.

We assume now that the welding operator has produced a satisfactory weld. By this, we mean a weld which has been made under suitable conditions (clean welding tips, good work sheet quality, etc.) and which passes any visual, mechanical or other test which he chooses to employ. Corresponding to this weld is a thermal signal function which we wish to duplicate in all later welds, even when the welding conditions change.

The operator then places the mode selector switch 505 in the automatic position. At this time, the digitally-stored set point voltage will be supplied to summing amplifier 501 during the course of the weld. Also, switch 506 will be closed unless a fail-safe signal is received at the end of the sample time. Furthermore (by means not shown), new set point values are prevented from entering the memory 504.

The set point value enters summing amplifier 501 as a constant, analog, negative bias voltage to be superimposed on the thermal signal. If a new weld is now made and yields the same thermal signal as before, the output of summing amplifier 501 will be passing through zero exactly at the end of the sample time. At that instant, switch 502 opens and switch 507 closes, a "zero" signal will pass through switch 507 and the welding power will continue at its previous level. However, if the new weld causes a lower sampled thermal signal than before, a correction voltage enters summing amplifier 508. There, it is combined with the current control voltage from potentiometer 511 in such a way as to increase the effective control power. The reverse is true if a higher thermal signal is seen at the end of the sample time. The amount of the change in control power for a given error signal depends upon the gain settings of several amplifiers. Thereafter, the weld proceeds at a new power level just as though the welding current control 511 had automatically and instantly been set to a new position. At the end of the weld, the system resets itself.

Figure 6:
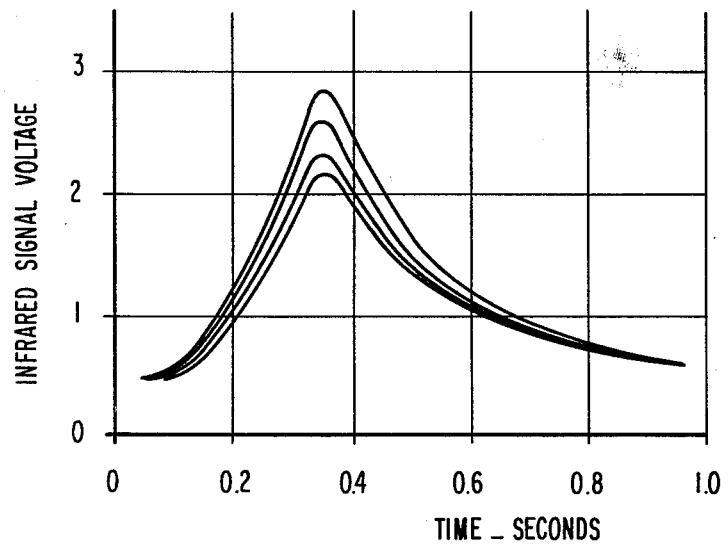
FIG. 6 is a graph illustrating the thermal signatures for four welds made at different heating rates.

It is important to point out that this system does not measure the weld temperature itself. However, the detector output signal bears a strong relationship to the way in which the weld temperature rises and falls during weld formation, except for a small time delay due to the finite heat conduction time through the intervening metal. We have observed that the rise and fall of the detector signal are repeatable when identical welds are formed, and that they vary from weld to weld when non-identical welds are formed. Several typical thermal signatures for welds are shown in FIG. 6. These are oscilloscope traces of the rectified, amplified detector output signals, versus time, in response to the heating and cooling process during the formation of four typical welds made at slightly different values of the welding power.

In FIG. 6, we notice that the differences in the thermal signatures can be detected early in the welding cycle, long before the final temperature values are reached. (In this oscillogram, welding power was applied at the left edge of the traces.) Thus, there is sufficient time for an electronic system to detect the differences and to take corrective action so that the final temperatures are more nearly alike. Indeed, that is what is done in the embodiment of our invention where an instantaneous change in the welding power is brought about if, at a certain time early in the welding cycle, the thermal signal is above or below a certain standard value. In addition, the welding duration is automatically shortened or prolonged until a predetermined threshold value is reached by the thermal signal. The purpose here is to reduce any small differences in final temperatures in case the power correction is not fully effective.

Figure 8:
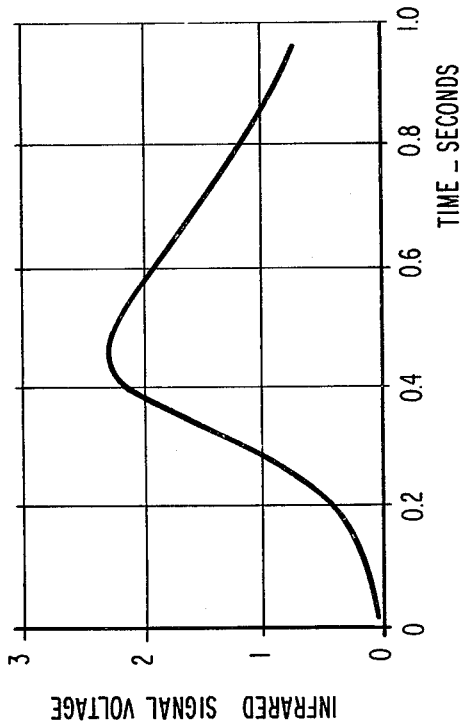
FIG. 8 is a graph showing the thermal histories of three welds made in an identical manner as those represented by FIG. 7 but with the use of the control of the present invention.
Figure 7:
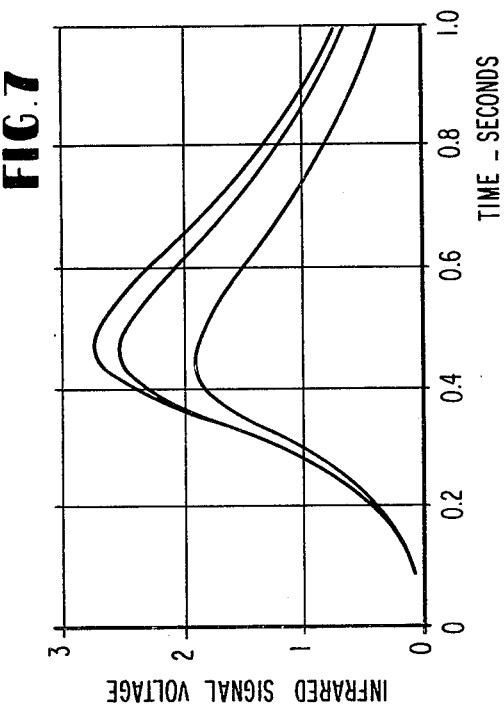
FIG. 7 is a graph showing the thermal histories of three ordinary welds which were made close to each other on the same work sheets, one after the other.

We illustrate this with the oscilloscope traces of FIGS. 7 and 8. The former shows the histories of three welds made under normal conditions, without the benefit of our invention. The latter shows the results of automatic control in which the same welds were repeated; their thermal histories now appear as a single trace.

In the preferred embodiment of our invention, the power correction is achieved by phase control of a pair of ignitrons in the welding machine. The timing is under the control of the welding current control potentiometer on the control panel. This is a normal mode of operation in many welding machines where the welding power is varied by a change in timing instead of a change in voltage amplitude.

In our preferred embodiment, the welding power change is brought about by an automatic adjustment of the timing signals which are being sent to the ignitrons from the welding current control. However, our invention contemplates any means in which the effective electrical power in the weld is automatically varied. As is known to welding-controller design engineers, other methods of welding-current control are possible besides phase control. We intend our method of thermal sensing and power correction to be applicable to all of these methods.

What is claimed is:

1. A method of automatically operating a spot welder comprising the steps of:
   during each weld measuring the temperature produced within one of a pair of welding tips to produce a thermal signal proportional to the temperature of the weld instant by instant;
   sampling said thermal signal and digitally storing a value corresponding to the sampled thermal signal produced for a good weld; and
   thereafter, comparing said thermal signal with a signal proportional to the stored digital value to generate a control signal for controlling the welding power of said spot welder during each weld.

2. The method according to claim 1 wherein said step of measuring is performed by optically conducting infrared radiation from a hole in said one of a pair of welding tips to an infrared detector.

3. A control system for a spot welder having a pair of welding tips which are brought into contact with material to be welded, said control system comprising:
   a flexible optical fiber bundle, one end of which is positioned in a hole in one of said pair of welding tips, said hole projecting toward a contact face of the one welding tip;

an infrared detector located remotely from said one welding tip, the other end of said flexible optical fiber bundle being positioned to direct radiation emanating from the bottom of said hole in said one welding tip onto said infrared detector, said infrared detector producing a thermal signal proportional to the temperature of a weld being made instant by instant;

means for selectively sampling said thermal signal and digitally storing a value corresponding to the sampled thermal signal; and means for selectively comparing said thermal signal with a signal proportional to the stored digital value to generate a control signal for controlling the welding power of said spot welder.

4. The control system according to claim 3 further comprising mode selection means for exclusively selecting for operation one or the other of said means for selectively sampling and digitally storing, and said means for selectively comparing.

* * * * *